(12) United States Patent
George

(10) Patent No.: US 10,105,043 B2
(45) Date of Patent: Oct. 23, 2018

(54) SPECULA

(76) Inventor: Samuel George, Weybridge (GB)

(*) Notice: Subject to any disclaimer, the term of this patent is extended or adjusted under 35 U.S.C. 154(b) by 952 days.

(21) Appl. No.: 13/882,362

(22) PCT Filed: Oct. 31, 2011

(86) PCT No.: PCT/GB2011/052119
§ 371 (c)(1),
(2), (4) Date: Oct. 2, 2014

(87) PCT Pub. No.: WO2012/056254
PCT Pub. Date: May 3, 2012

(65) Prior Publication Data
US 2015/0057502 A1    Feb. 26, 2015

(30) Foreign Application Priority Data

Oct. 29, 2010 (GB) .................................. 1018276.4

(51) Int. Cl.
*A61B 1/32* (2006.01)
*A61B 1/303* (2006.01)

(52) U.S. Cl.
CPC ............... *A61B 1/32* (2013.01); *A61B 1/303* (2013.01)

(58) Field of Classification Search
CPC ................................... A61B 1/303; A61B 1/32
USPC ................................................ 606/219–225
See application file for complete search history.

(56) References Cited

U.S. PATENT DOCUMENTS

| 3,110,305 | A | * | 11/1963 | Sygnator | A61B 1/32 600/222 |
| 5,072,720 | A | * | 12/1991 | Francis | A61B 1/32 600/186 |
| 5,868,688 | A | * | 2/1999 | Avidor | A61H 7/004 601/102 |
| 6,024,696 | A | | 2/2000 | Hoftman | |
| 6,379,299 | B1 | * | 4/2002 | Borodulin | A61B 1/32 600/215 |
| 6,416,466 | B1 | * | 7/2002 | Hsiao | A61B 1/32 600/220 |
| 7,070,561 | B1 | * | 7/2006 | Ansari | A61B 1/32 600/220 |
| 2002/0022771 | A1 | * | 2/2002 | Diokno | A61B 1/32 600/220 |
| 2002/0169363 | A1 | | 11/2002 | Herold | |
| 2007/0255110 | A1 | * | 11/2007 | Wax | A61B 1/303 600/223 |
| 2009/0099422 | A1 | * | 4/2009 | George | A61B 1/32 600/214 |

(Continued)

FOREIGN PATENT DOCUMENTS

| GB | WO2006064247 A2 | 6/2006 |
| WO | WO0147406 A1 | 7/2001 |
| WO | WO2009158435 A1 | 12/2009 |

*Primary Examiner* — Matthew Lawson
(74) *Attorney, Agent, or Firm* — Thomas C. Saitta

(57) ABSTRACT

A vaginal speculum comprises upper and lower blades arranged to pivot relative to each other about coupling elements each associated with a respective blade. The upper blade is detachable from the lower blade, when the speculum is in situ in the vaginal cavity, upon pulling the upper blade generally proximally. This decouples the coupling elements from each other or detaches at least one of the coupling elements from the associated blade. The speculum has optional side blades.

22 Claims, 8 Drawing Sheets

(56) References Cited

U.S. PATENT DOCUMENTS

2011/0301424 A1\* 12/2011 Steigerwald ........... A61B 1/303
                                                        600/235

\* cited by examiner

SPECULA

The present invention relates to a speculum, and in particular to a vaginal speculum for enabling examination and treatment of the vaginal walls, cervix and uterus.

As is generally known, vaginal specula are used by physicians for dilating the opening of the vaginal cavity in order that the vaginal walls and cervix may be more easily visible and accessible.

Typical bivalve specula such as Cusco's speculum comprise two blades—an upper blade and a lower blade—joined near their proximal ends by a fixed hinge. A handle depends from the proximal end of at least one of the blades for a physician to hold. The proximal end portions of the blades together define a proximal aperture, through which the physician may observe and access the vaginal cavity and cervix with instruments for inspection, investigation or surgery. Each blade has an associated handle and the handles can be moved relative to one another to open or close the blades.

In use, the speculum is positioned in the vaginal cavity so that the upper blade is against the top of the vaginal cavity and the lower blade is against the bottom of the vaginal cavity. The blades are then splayed apart by operation of the handles to dilate the vaginal cavity by pressing apart its top and bottom walls. In view of the fixed hinge, the dilation of the vaginal cavity is greatest at the distal ends of the blades and decreases towards their proximal ends when the blades are fully open.

Although the bivalve speculum is effective in widening the cervical end of the vaginal cavity by splaying apart the blades, access remains restricted by the diameter of the proximal aperture. Better access may be required during some treatments such as surgical procedures or in order to use certain medical instruments. Thus, it may be preferred to use a single-bladed speculum such as Sim's speculum or Auvard's weighted speculum rather than a bivalve speculum during certain gynaecological procedures.

Unfortunately, with a single-bladed speculum it is difficult to locate the cervix to grab it with a tenaculum, especially if there is laxity of the vaginal wall or if the cervix extends beyond the speculum's reach. This requires the physician to use variously-sized specula or a speculum and a retractor at the same time, or to ask an assistant to help retract tissues while trying to locate the cervix.

It is quite common that after succeeding in holding the cervix with a tenaculum and pulling on the tenaculum to bring the cervix into view, a single-bladed speculum slips out and falls down to the floor and the vaginal opening closes up on itself, obstructing the view to the cervix. This is extremely frustrating and can happen repeatedly during the same operation, resulting in an assistant holding the speculum in place by pushing it in and downwards against the patients perineum.

The use of multiple instruments and/or an assistant increases the cost of gynaecological procedures and makes such procedures more complicated and lengthy to perform.

A further problem is that in order to hold and operate the speculum, the physician's or assistant's hands and fingers are often in contact with, or in close proximity to, the patient's genitalia, upper thighs and buttocks during a gynaecological procedure. This may be distressing to the patient and may even lead to accusations of impropriety against the physician or the assistant.

It is against this background that the present invention has been devised.

In one sense, the invention resides in a speculum for dilating a body cavity, the speculum comprising upper and lower blades arranged to pivot relative to each other about coupling elements each associated with a respective blade; wherein the upper blade is detachable from the lower blade, when the speculum is in situ in the cavity, upon pulling the upper blade generally proximally to decouple the coupling elements from each other or to detach at least one of the coupling elements from the associated blade.

The invention can also be expressed in method terms as a method of removing an upper blade of a speculum having upper and lower blades pivotably coupled to each other by respective associated coupling elements, the method comprising pulling the upper blade generally proximally to decouple the coupling elements from each other or to detach at least one of the coupling elements from the associated blade.

Thus, embodiments of the invention avoid the problems of the prior art by providing a bivalve speculum that can be easily dislocated within the vagina to become a single-bladed speculum after locating and holding the cervix with a tenaculum. This dislocation of the bivalve speculum within the vagina avoids the problems associated with the laxity of the vaginal wall and locating the cervix. Moreover, the speculum can be held in place throughout the procedure by the use of one or more of a stitch, a tenaculum, a weight or an elasticated adhesive band connected across a patient's perineum.

The upper blade is suitably detachable from the lower blade by moving the upper blade in a direction perpendicular to a pivot axis defined by the coupling elements. It is preferred that the upper blade is detachable from the lower blade solely by pulling the upper blade away from the lower blade, with no prior unfastening operations such as undoing screws or clamps being necessary to effect detachment.

At least one of the coupling elements may define the direction of movement for detaching the upper blade from the lower blade. For example, the coupling element of one of the blades may define a path, in which case the coupling element of the other of the blades is a path-follower arranged to follow the path in a decoupling direction, preferably toward an open end of the path. Advantageously, at least a portion of the path is inclined relative to the length of the associated blade upwardly and proximally when the speculum is oriented for use with the associated blade extending generally horizontally.

The inclined path provides a detent arranged to resist decoupling or detachment of at least one of the coupling elements, whose resistance must be overcome to effect decoupling or detachment. In this example, the upper blade is guided to move upwardly when pulled proximally to decouple the coupling elements.

A retainer feature may be provided to hold together the upper and lower blades before use. Such a feature may comprise complementary inter-engaging formations on the upper and lower blades that engage with each other when the speculum is in a closed state. It is also possible to have a removable or breakable retainer extending between the upper and lower blades.

Side blades may be added, these being positioned to resist inward movement of a wall of the cavity between the upper and lower blades when the speculum is in an open state. The side blades may be removable. Preferably, the side blades are coupled to the lower blade, for example via the coupling element associated with the lower blade. More generally, a coupling element associated with the upper blade or the lower blade may be a spigot and a side blade may be attached to the spigot, for example by a stud-like protrusion of the side blade that fits into a cavity of the spigot.

Advantageously, at least one of the side blades may comprise a proximal lever for controlling pivotal upward or downward movement of the side blade when the speculum is in situ in the cavity. This concept may be expressed independently as a speculum for dilating a body cavity, the speculum comprising: upper and lower blades arranged to pivot relative to each other; and side blades positioned to resist inward movement of a wall of the cavity between the upper and lower blades when the speculum is in an open state; wherein at least one of the side blades comprises a proximal lever for controlling pivotal upward or downward movement of the side blade when the speculum is in situ in the cavity.

The side blades may be provided on an inner side of the upper and lower blades. Again, this concept may be expressed independently as a speculum for dilating a body cavity, the speculum comprising upper and lower blades movable relative to each other; and side blades connected or connectable to an inner side of at least one of the upper and lower blades and being arranged to extend laterally from between the upper and lower blades when the upper and lower blades are moved apart.

For example, the side blades may have a proximal root portion connected or connectable to an inner side of an upper or lower blade and a distal free end portion that moves laterally relative to the root portion. Preferably, in that case, the free end portion moves laterally by virtue of resilience of the side blade. For that purpose, the side blade may have a shape, set or curvature that deforms elastically to fit the free end portion between the upper and lower blades when those blades are closed together and that recovers elastically to move the free end portion laterally from between the upper and lower blades when those blades are moved apart into an open state. For example, the free end portion may be outwardly inclined relative to the root portion in a distal direction.

The speculum of the invention suitably comprises an attachment feature on the lower blade for connecting the lower blade, in use, to body tissue within the cavity. That attachment feature is preferably at or near a distal end of the lower blade. The attachment feature may, for example, be a hole for attachment of a stitch extending into body tissue such as the cervix. Alternatively, the attachment feature may be an aperture for receiving a protruding part of the body tissue or for accommodating a tenaculum extending through the aperture to the body tissue.

A connector may be provided for connecting an external biasing element such as a weigh or a strap to apply a downward biasing force to the lower blade. It is also possible for the speculum to have integral added weight for this purpose. In either case, it is preferred for the connector or the weight to be on a handle extending at an acute angle from the lower blade.

Each of the upper and lower blades suitably has a respective handle, in which case a locking mechanism preferably acts between the handles to hold the blades open against inward pressure from the cavity. Advantageously, that locking mechanism comprising a ratchet formation that is movable by a user to release the locking mechanism and to free the blades for relative movement.

A line of weakness may be provided between at least one of the coupling elements and the associated blade. The upper blade can then be detached from the lower blade by detaching that coupling element from the associated blade along the line of weakness.

Thus, the invention provides a bivalve speculum that can easily be reconfigured into a single-bladed speculum during a procedure, for example after the cervix has been located and held. As such, only a single speculum is required due to the adaptability of the speculum. Advantageously, the speculum of the invention enables improved access to locate and hold the cervix and thereafter enables improved access to the cervix and uterus once the cervix is held.

The bivalve speculum has just two blades in some embodiments of the invention, but in other embodiments the bivalve speculum is provided with supplementary side blades or retractors. References in this specification to a bivalve speculum or to a speculum having two blades are not intended to exclude specula having upper and lower primary blades and optionally also one or more additional supplementary blades such as side blades or auxiliary blades that vary the length of the primary blades. Also, it is possible for such supplementary blades to remain attached to the lower primary blade of the speculum, which remains in the vagina after the upper primary blade has been removed. Embodiments of the invention therefore provide a single-bladed speculum that may have integral side blades. Thus, references in this specification to a single-bladed speculum are not intended to exclude specula having a primary blade and one or more additional supplementary blades.

Embodiments of the invention provide a speculum that is arranged to be attached to the cervix in order to prevent the speculum slipping out of the vagina. Additionally or alternatively, a weight may be attached to the speculum to keep the speculum steady and help to prevent the speculum slipping out of the vagina, in which case the speculum may have an attachment point for such a weight.

The speculum in preferred embodiments of the invention requires no nuts or screws to be turned in its operation; the speculum is therefore simple and quick to use. The speculum can easily be operated by a single physician with little manipulation and without the need for an assistant.

The speculum of the invention can be used with or without suction.

Exemplary embodiments of the present invention will now be described with reference to the drawings, in which.

Throughout the following description, like reference numerals refer to like parts.

Figure 1:
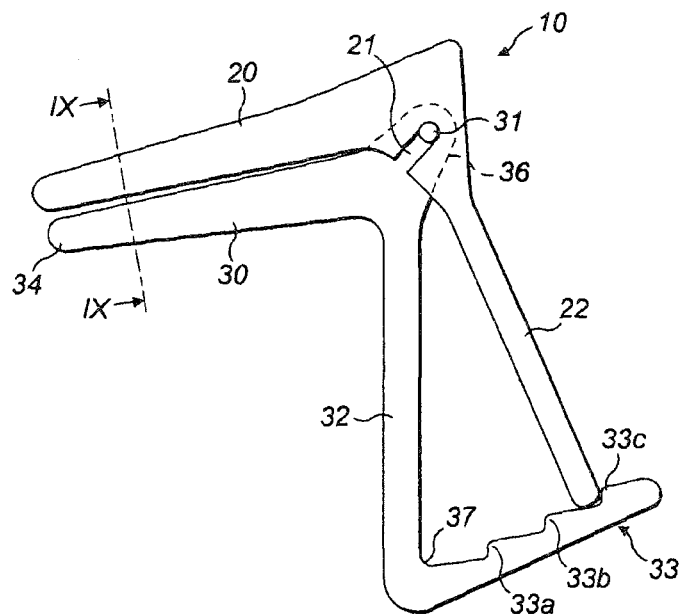
FIG. 1 is a side view of a speculum in an assembled state according to a first embodiment of the invention.
Figure 2:
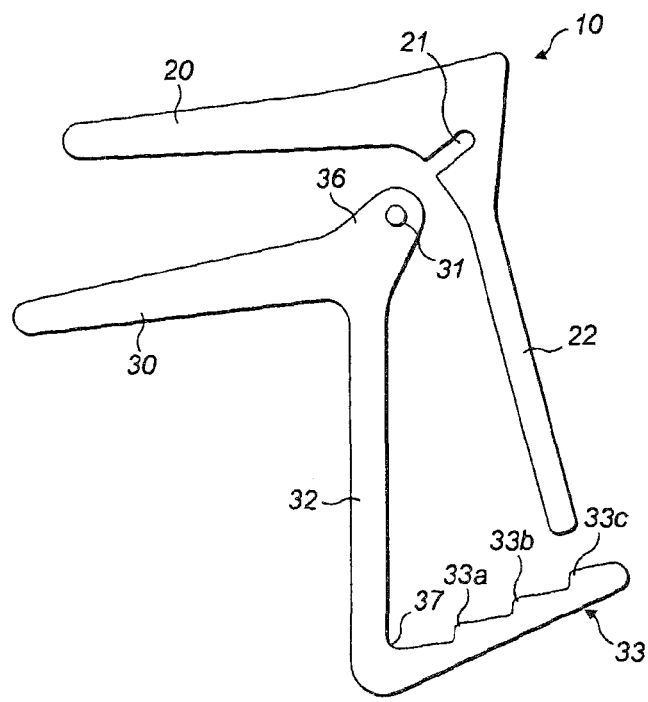
FIG. 2 is a side view of the speculum of FIG. 1 in a disassembled state.

Initially, a speculum 10 in accordance with a first embodiment of the invention will be described with reference to FIGS. 1 to 4.

The speculum 10 is a bivalve duckbill speculum that is arranged to be adapted easily into a single-bladed speculum when in situ. The speculum 10 has an upper blade 20 and a lower blade 30 that are pivotally coupled to one another by respective coupling elements 21, 31. Whilst the speculum 10 could be re-usable and made of steel, it is preferably disposable and made of injection-moulded plastics.

Each of the upper and lower blades 20, 30 has a respective handle 22, 32. The handle 32 of the lower blade 30 extends downwardly and distally away from the coupling element 31 at an acute angle to the lower blade 30, while the handle 22 of the upper blade 20 extends downwardly and proximally away from the coupling element 21 at an obtuse angle to the upper blade 20. The differing angles of the handles 22, 32 with respect to the blades 20, 30 allows the handles 22, 32 to be squeezed towards one another causing the blades 20, 30 to splay apart, pivoting about a pivot axis defined by the coupling elements 21, 31.

In use, the blades 20, 30 are initially arranged in a closed position with a minimal gap between them. Preferably the blades 20, 30 abut one another or are even interlocked with one another, as FIG. 9 will show. The speculum 10 is inserted into the vaginal cavity 50 (only shown in FIG. 4) with the blades 20, 30 in the closed position. Then, the handles 22, 32 are squeezed together so that the blades 20, 30 splay and as a result push the vaginal walls 51 apart. This dilation of the vaginal cavity provides improved visibility and access, particularly for the purpose of locating and holding the cervix with an instrument such as a tenaculum.

The handles 22, 32 of the speculum 10 have a ratchet arrangement that prevents the blades 20, 30 moving together under inward force from the vaginal walls. The ratchet arrangement comprises a ratchet arm 33 that extends proximally from the lower end of the handle 32. As best illustrated in FIG. 1, the ratchet arm 33 preferably has a radius of curvature centred on the pivot axis defined by the coupling elements 21, 31. The ratchet arm 33 has a series of teeth 33a, 33b, 33c that engage with the end of the handle 22 of the upper blade 20. Hence, as the handles 22, 32 are squeezed together, the end of the handle 22 of the upper blade 20 will successively engage with respective teeth 33a, 33b, 33c of the ratchet arm 33 associated with the handle 32 of the lower blade 30.

When the speculum 10 is in the open position, in situ within the vaginal cavity, the physician is then able to locate and hold the cervix 52. The dilation of the cervical end of the vaginal cavity 50 provided by the speculum 10 makes location of the cervix 52 easier. A tenaculum can then be inserted through interior of the speculum 10 to hold the cervix 52.

Once the cervix 52 is located and retained, the physician can connect the cervix 52 to the lower blade 30 of the speculum 10, if desired. For this purpose, the lower blade 30 is provided with a cervix attachment in the form of a hole 34 near a distal end of the lower blade 30. In use, when the speculum 10 is in the open position within the vaginal cavity 50, a stitch 35 can be passed through the hole 34 and through the cervix 52 to connect the lower blade 30 to the cervix 52.

Alternatively, a slot, rather than a hole, can be provided in the lower blade 30 through which a portion of the cervix 52 protrudes. A tenaculum can then be used to hold the protruding part of the cervix 52 in position. Another possibility is for the tenaculum to extend through a hole or slot in the distal end portion of the lower blade 30 to grasp the cervix 52 distally beyond that hole or slot. In both cases, the tenaculum helps to retain the lower blade 30 in the vaginal cavity when the tenaculum is attached to the cervix 52.

By virtue of the invention, the speculum 10 can then be converted from a bivalve configuration to a single-bladed configuration as discussed below.

The coupling elements 21, 31 are arranged so that the coupling elements 21 of the upper blade 20 can disengage from the coupling elements 31 of the lower blade 30. Since the speculum 10 is in situ in the vaginal cavity 50, the coupling elements 21, 31 are arranged so that as the upper blade 20 is pulled generally proximally in a direction perpendicular to the pivot axis, the coupling elements 21, 31 decouple and the upper blade 20 is separated from the lower blade 30. The upper blade 20 then easily slides out from the vaginal cavity 50. Hence, the upper blade 20 can both be disengaged from the lower blade 30 and removed from the vaginal cavity 50 in a single sliding movement with minimal manipulation.

Figure 3:
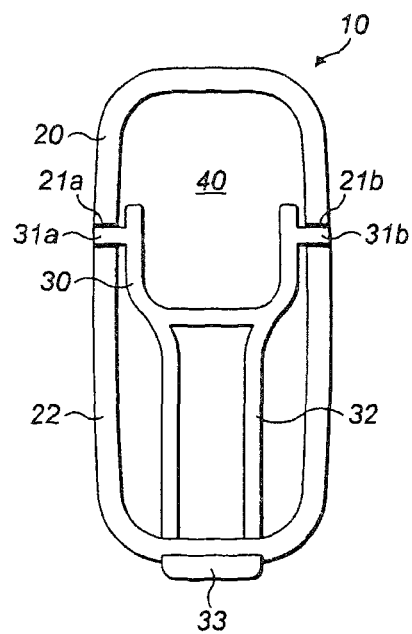
FIG. 3 is a rear view of the speculum of FIG. 1, as would be seen by an physician of the speculum when the speculum is in situ.
Figure 4:
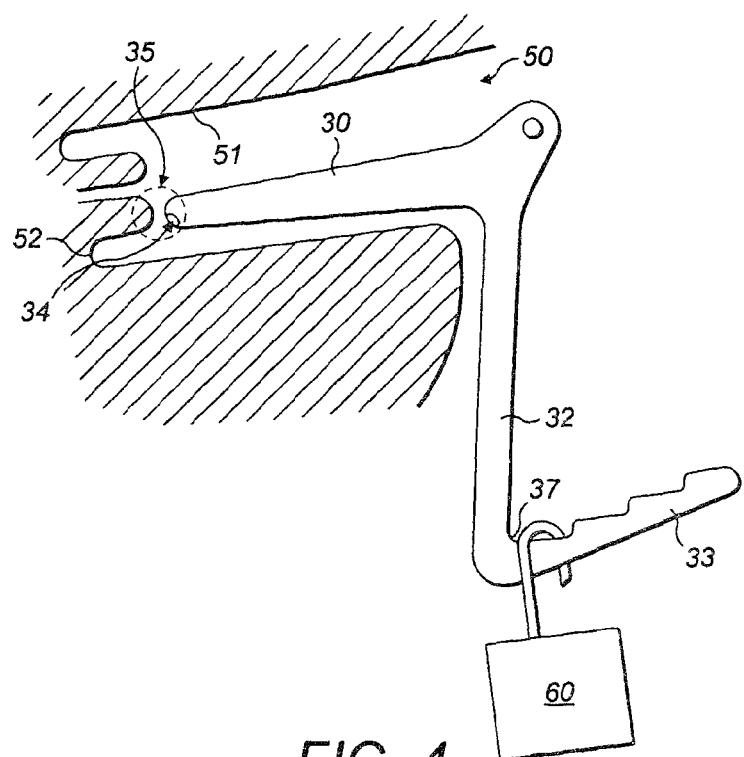
FIG. 4 is a sectional side view of the speculum of FIG. 1, in situ, after transforming the bivalve speculum into a single-blade speculum.

As will be appreciated from FIG. 3, both the upper and lower blades 20, 30 are provided with left coupling elements 21a, 31a and right coupling elements 21b, 31b. In the embodiment shown, the coupling elements of the upper blade 20 are slots 21a, 21b, and the coupling elements of the lower blade are spigots 31a, 31b that are a sliding fit in the slots.

The spigots 31a, 31b extend laterally outwardly from respective pivot supports 36 of the lower blade 30 protruding upwardly and proximally from the lower blade 30 and are aligned with one another so that they define the pivot axis. The pivot supports 36 lie within and between side walls of the upper blade 20. The spigots 31a, 31b are preferably cylindrical, for sliding engagement with the slot and a smooth pivoting action.

Each of the slots 21a, 21b extends generally proximally from an open end at a distal edge of a respective side portion of the upper blade 20 to a closed end within that side portion of the upper blade 20. The slots 21a, 21b have a width that is slightly greater than the diameter of the corresponding spigots 31a, 31b. This provides a close fit between the slots 21a, 21b and spigots 31a, 31b while also allowing for relative sliding movement of the spigots 31a, 31b with respect to the slots 21*a*, 21*b*. The slots 21*a*, 21*b* are straight and are substantially longer than they are wide.

The slot 21 is oriented at an angle with respect to the length of the upper blade 20 to discourage accidental disengagement of the blades 20, 30. In particular, the slot 21 has a slight upward slant moving proximally from its open end toward its closed end so that the weight of the upper blade 20 holds the spigot 31 in the slot 21 when the speculum 10 is oriented for use. The inward force exerted on the speculum 10 by the vagina when the speculum 10 is in bivalve mode will also exert a downward force on the upper blade 20 to hold it in engagement with the lower blade 30 by virtue of the angle of the slot 21.

In order to decouple the coupling elements 21, 31, the angle of the slot 21 means that a slight upward movement of the upper blade 20 is required to overcome the forces holding the blades 20, 30 together. Hence, when removing the upper blade 20 from the lower blade 30, a force in a slightly upward and proximal direction is applied to the upper blade 20. The specific angle and length of the slot 21 is chosen to minimise the likelihood of accidental disengagement of the blades 20, 30 while ensuring that the blades are still easily separable, in situ, while minimising discomfort to the patient.

When the upper blade 20 has been removed from the vaginal cavity 50, the lower blade 30 remains within the vaginal cavity 50 joined to the cervix 52. Optionally, a bias element such as a weight 60 can then be attached to the handle 32 of the lower blade 30 near its junction with the ratchet arm 33 in order to exert a downward force on the lower blade 30. This in turn forces the lower blade 30 downwards, which helps to hold the lower blade 30 within the vaginal cavity 50 while also dilating the vaginal cavity 50.

The acute angle of the handle 32 of the lower blade 30 facilitates reliable location of the lower blade 30 within the vaginal cavity 50, as the weight force applied near the downward and forward end of the handle 32 pushes the lower blade 30 into the vaginal cavity. It will be noted in this respect that as the vaginal opening faces slightly upwardly when the patient is in the lithotomy position typically employed in gynaecological procedures, the lower blade 30 faces slightly downwardly in the distal direction in use. References elsewhere in this specification to the lower blade 30 facing generally horizontally are not intended to exclude such inclination.

The lower blade 30 of the speculum 10 has a weight-hanging feature in the form of a hook 37 on the handle 32 near its junction with the ratchet arm 33. Alternative weight-hanging features include a slot or hole incorporated into in the handle 32 around the same location, to which a weight may be hooked or otherwise attached. Alternatively, added weight may be integrated into one or more of the handles 22, 32 and/or the ratchet arm 33, for example by thickening, although this option is best reserved for when the speculum 10 is made of metal. Another biasing option is a strap acting between the lower blade 30 of the speculum 10 and an anchor, which may be provided instead of a weight to apply a downward biasing force on the lower blade 30.

The first embodiment of the present invention therefore provides a bivalve speculum that is easily reconfigured into a single-blade speculum. This arrangement has the advantages associated with single-bladed speculums of improved access to the vaginal cavity, while also enabling easier location of the cervix and connection of the lower blade to the cervix by the initial use of a bivalve configuration.

Figure 5:
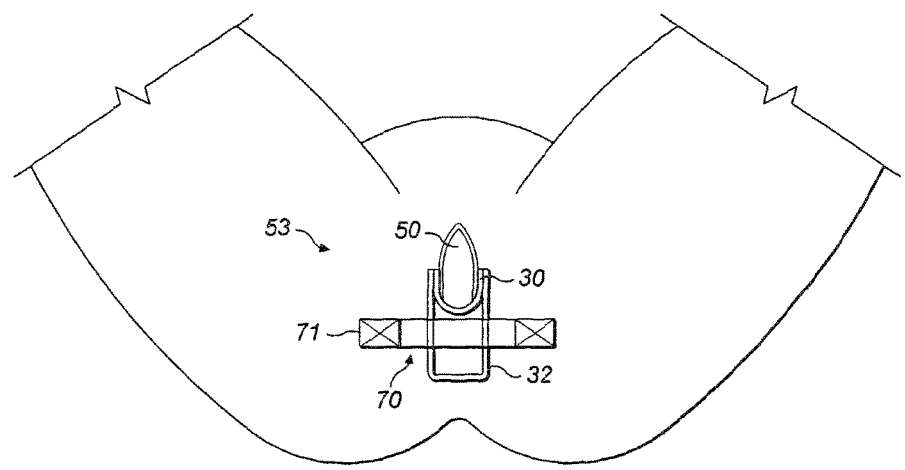
FIG. 5 is a rear view of the speculum of FIG. 1 in situ, after transforming the bivalve speculum into a single-blade speculum, with adhesive tape optionally attaching the speculum to the patient's perineum.

FIG. 5 is a rear view of the lower blade 30 in situ, after transforming the bivalve speculum into a single-blade speculum. To prevent the lower blade 30 slipping out of the vagina, a tape 70 is attached across the handle 32 of the lower blade 30 and is stuck to the patient's perineum 53 to hold the lower blade 30 in position. The tape 70 is preferably an elasticated tape with adhesive tabs 71 at each end for connecting to the perineum 53. The adhesive tape 70 can be used in conjunction with the aforementioned stitching of the lower blade 30 to the cervix 52 and/or the weight arrangement, or on its own.

Figure 6:
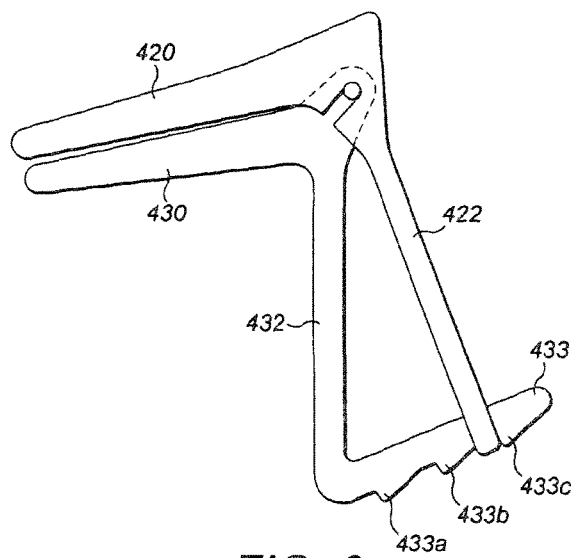
FIG. 6 is a side view of an alternative embodiment of the invention in which a ratchet arrangement is provided on a lower surface of a ratchet arm.

FIG. 6 illustrates an alternative embodiment of the invention in which the teeth of the ratchet arm 433 are provided on a lower surface of the ratchet arm 433. Hence, as can be seen in FIG. 6, teeth 433*a*, 433*b*, 433*c* are provided on a lower, rather than an upper, surface of the ratchet arm 433. In this embodiment of the invention, the handle 422 of the upper blade loops beyond and below the ratchet arm 433 to engage with the teeth 433*a*, 433*b*, 433*c* on the lower surface of the ratchet arm 433.

In the arrangement of FIG. 6, the teeth are suitably shallower than the teeth provided in the first embodiment of the invention to allow for easy dislocation and separation of the upper and lower blades of the speculum.

Figure 7:
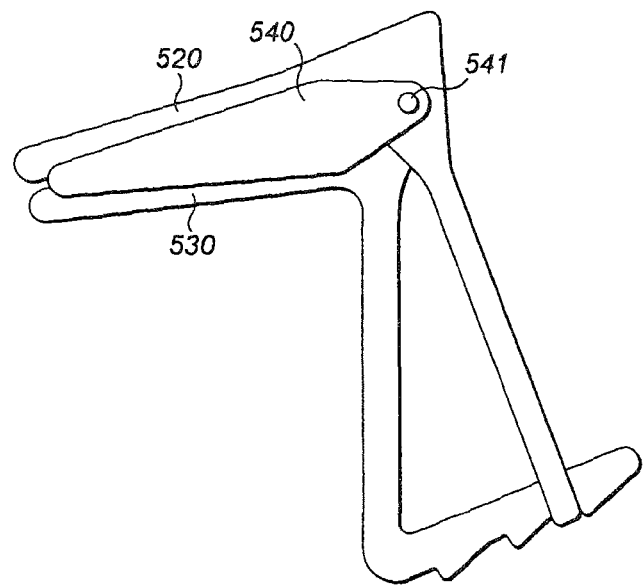
FIG. 7 is a side view of a four-blade speculum comprising a bivalve arrangement of primary upper and lower blades fitted with supplementary side blades in a variant of the embodiment shown in FIG. 6.

The speculum 10 may optionally be provided with side blades 540 to form a four-bladed speculum, as shown in FIG. 7. As explained previously, such a speculum is still regarded as fundamentally a bivalve speculum as it has primary upper and lower blades 20, 30 and the side blades 540 are merely auxiliary or supplementary. The side blades 540, of which only one is visible in the side view of FIG. 7, are provided one each side of the upper and lower blades 20, 30 and are connected to the lower blade 30 via the spigot 541 that connects the upper and lower blades 20, 30.

For example, a spigot 541 may be a hollow tube and the associated side blade 540 may have a pin or stud that snap-fits into the tubular spigot 541; alternatively the side blade 540 may simply have a hole that receives the spigot 541, which then need not be tubular and may be solid. Alternatively, a separate connection element such as a rivet could be provided to attach the side blade 540 to the remainder of the speculum 10. In any event, it is desirable for the side blades 540 to be easily removable when the speculum 10 is outside the vaginal cavity, if a physician determines that the additional support of the side blades 540 is not necessary for a particular patient.

The side blade arrangement is similar to that described in my previous International patent application WO 2006/064247, such that movement apart of the upper and lower blades 520, 530 drives the side blades 540 to pivot laterally outwardly to dilate or support the vaginal cavity. Hence, the side blades 540 help to increase dilation of the vaginal cavity or at least to prevent it narrowing, and so help to prevent inward collapse of the vaginal side walls between the opened upper and lower blades 520, 530.

Figure 8:
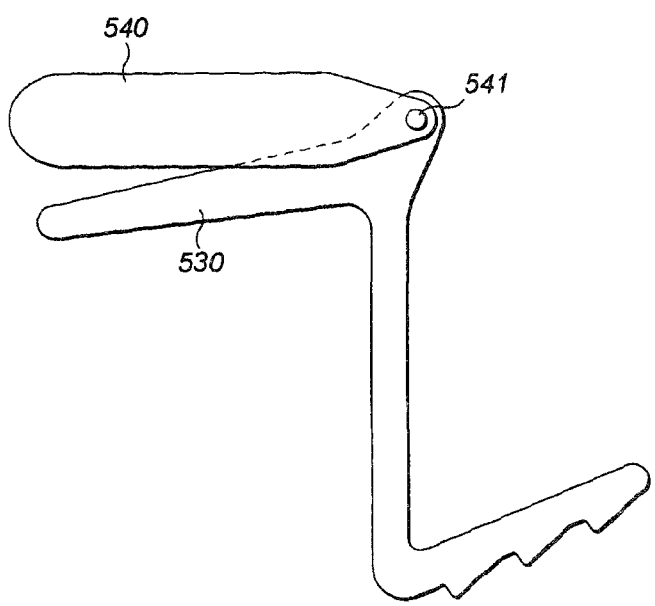
FIG. 8 is a side view of a four-blade speculum after removal of the upper blade to leave a three-blade speculum comprising a lower blade and two supplementary side blades.

Since the side blades 540 are connected to the lower blade 530 via the spigot 541, the upper blade 520 can be removed from its engagement with the spigot 541 to leave a single-bladed speculum with side blades 540 attached to the lower blade 530. Again, only one of the side blades 540 is visible in this side view. An example of this is shown in FIG. 8, which shows a variant in which ratchet teeth are provided on an upper surface of the ratchet arm.

As a further optional feature of the invention, a retainer may be provided for holding the upper and lower blades together during transportation and storage. This reduces the risk that unwanted separation of the blades could occur prior to use. For example, as shown in FIG. 9, male/female interlocking engagement between the upper and lower blades 20, 30 holds the blades in a closed position during transportation and storage, or otherwise prior to use.

Figure 9:
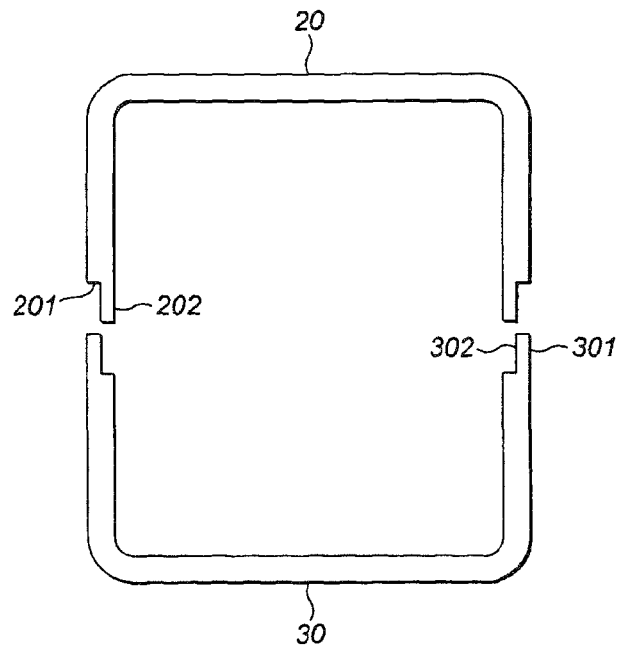
FIG. 9 is a cross-sectional view on line IX-IX of FIG. 1 showing optional interlocking formations for holding the blades together when in a closed position.

In FIG. 9, both the upper and lower blades 20, 30 are provided with complementary stepped mating edges. In particular, the upper blade 20 has a protrusion 202 that engages with a lower blade recess 302, and an upper blade recess 201 engages with a lower blade protrusion 301. This provides interlocking engagement that holds the blades 20, 30 together before use, but that can be overcome easily when the blades 20, 30 are opened by squeezing together their handles 22, 32.

In other arrangements to prevent the blades 20, 30 from separating before use, a band may be provided around the blades or a seal may be provided between the blades. Such a band or seal may be arranged to snap apart or detach to free the blades 20, 30 when a sufficient force is applied to the handles 22, 32. This operation could be carried out when the blades 20, 30 are inserted into the vagina but to avoid any risk of debris being left in the vagina, it preferably takes place before the blades 20, 30 are inserted into the vagina. Alternatively, a removable band or seal could hold the blades together. Breakage or removal of a band or seal indicates that the speculum has probably been used and so should not be used again.

Figure 10:
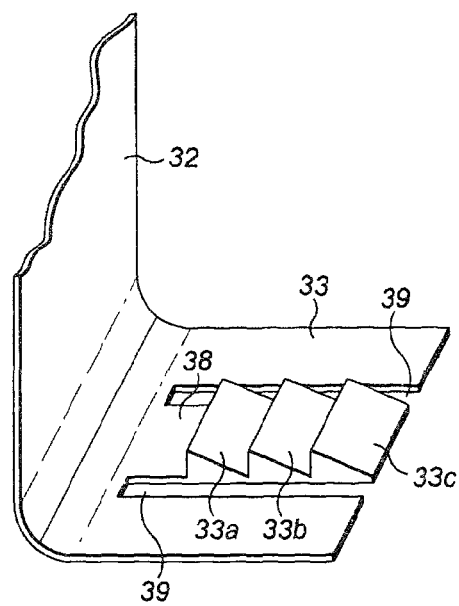
FIG. 10 is a detail perspective view of a ratchet arrangement for the speculum of FIGS. 1 to 4.
Figure 11:
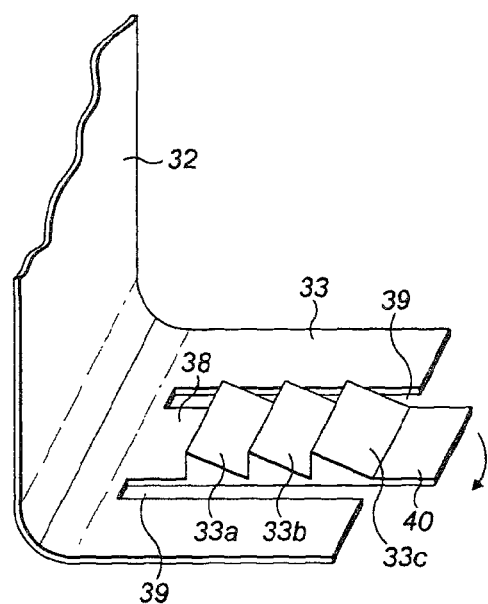
FIG. 11 is a detail perspective view of a variant of the ratchet arrangement shown in FIG. 10.

FIGS. 10 and 11 show details and variants of the ratchet arm 33 featured in the speculum 10 of FIGS. 1 to 4. These perspective views show the series of parallel transversely-extending teeth 33a, 33b, 33c on the upper side of the ratchet arm 33 that engage successively with the end of the handle 22 of the upper blade 20 as the handles 22, 32 are squeezed together. The teeth 33a, 33b, 33c are integrally moulded as part of a cantilever 38 defined between parallel slits 39 extending distally from the proximal end of the ratchet arm 33. The slits 39 free the cantilever 38 to deflect resiliently away from the pivot axis defined by the coupling elements 21, 31, allowing the end of the handle 22 to traverse the teeth 33a, 33b, 33c in a ratchet action as the handles 22, 32 are squeezed together.

The ratchet arm 33 shown in FIG. 11 has the further feature of a tab 40 at its free end whereby a physician may use a thumb or finger to deflect the cantilever 38 to release the end of the handle 22 from ratchet engagement with the teeth 33a, 33b, 33c. This allows the handles 22, 32 to move apart to close the blades 20, 30 of the speculum 10 or when removing the upper blade 20 from the lower blade 30.

Figure 12:
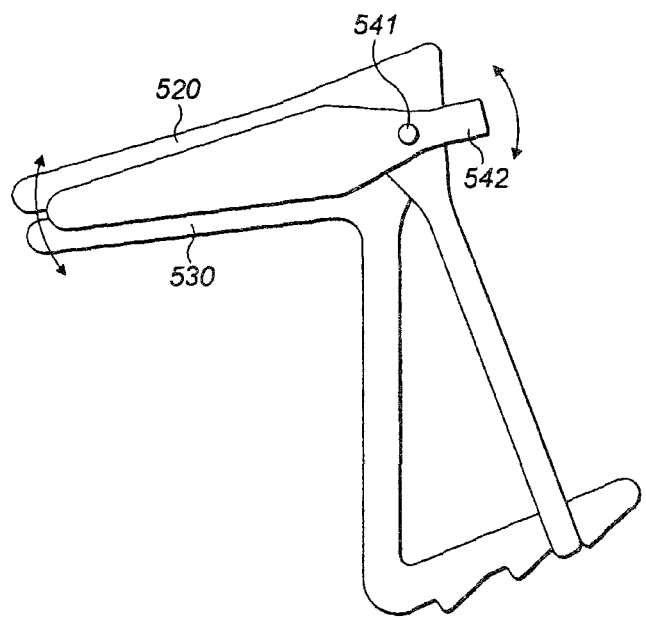
FIG. 12 is a side view of a four-blade speculum corresponding to FIG. 7 but showing additional control levers for pivotal movement of the side blades.

FIG. 12 illustrates a variant of the four-bladed speculum of FIG. 7, in which each side blade 540 has an integral control lever 542 extending proximally beyond the spigot 541. The control lever 542 can be moved up and down about the pivot axis defined by the spigot 541; in doing so, this causes the major portion of the side blade 540 on the distal side of the spigot 541 to swing in the opposite direction, i.e. down and up respectively.

The control levers 542 shown in FIG. 12 are useful to allow a physician to move the tips of the side blades 540 up and down relative to the remainder of the speculum, while the speculum is in situ within the vaginal cavity. For example, the side blades 540 may deflect differently upon opening such that their tips are not horizontally aligned, in which case the control levers 542 can be used to correct the misalignment if necessary. Conversely, the control levers 542 can be used independently to move the side blades 540 into an asymmetric arrangement if that is found to provide better support against inward collapse of the vaginal wall between the opened primary blades 20, 30, or to provide a better view of the cervix or vaginal wall.

Of course, use of a spigot 541 to hold a side blade 540 is not essential to the concept of control levers 542 shown in FIG. 12. For example, each side blade 540 may have a pin or stud that fits into a hole in the primary blades 20, 30, which hole need not necessarily be on the pivot axis about which the primary blades 20, 30 move relative to each other.

Figure 13:
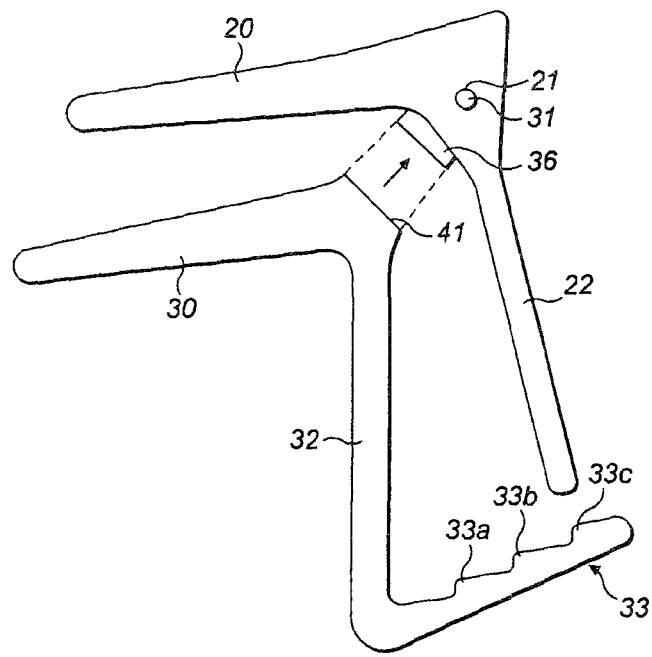
FIG. 13 is a side view that corresponds to FIG. 2 but shows another embodiment of the invention in which a coupling part of a hinge detaches from the associated blade to allow the upper blade to be detached from the lower blade.

FIG. 13 shows how a coupling part of a hinge may detach from the associated blade to allow the upper blade 20 to be detached from the lower blade 30. In this example, the coupling elements 21, 31 remain coupled but one of the coupling elements (in this case the spigot 31 with its associated pivot support 36) breaks free from its associated blade 20, 30 (in this case the lower blade 30) under a release force when the blades 20, 30 are intentionally separated.

Here, the spigots 31 fit in holes 21 as opposed to slots to define a pivot, and lines of weakness 41 are provided across the pivot supports 36 disposed distally with respect to the spigots 31. The lines of weakness 41 may, for example, be defined by perforations, grooves, notches or score lines. They enable the pivot supports 36, with the spigots 31 attached, to part easily from the lower blade 30 when the upper blade 20 is pulled proximally, while the spigots 31 remain in the holes 21.

Figure 14:
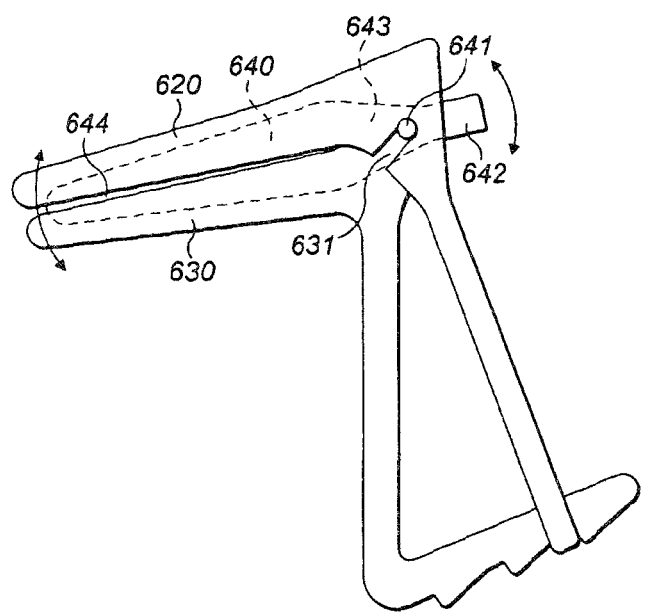
FIG. 14 is a side view that corresponds to FIG. 12 but shows an alternative embodiment of the invention in which the side blades are provided on an inner side of the upper and lower blades.
Figure 15:
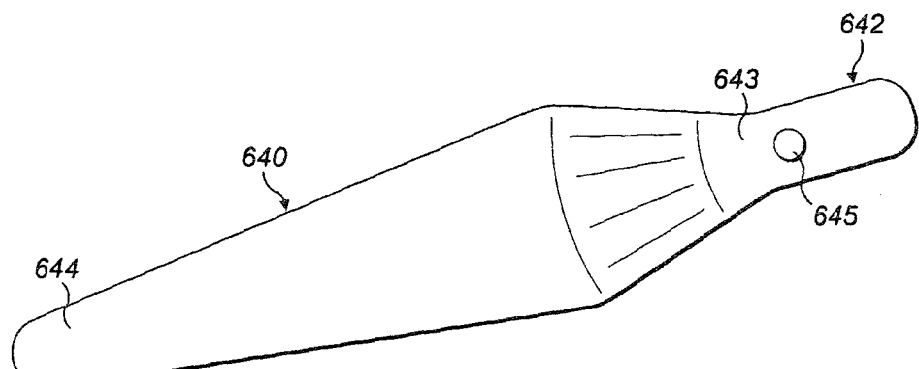
FIG. 15 is a side view of one of the side blades shown in FIG. 14.
Figure 16:
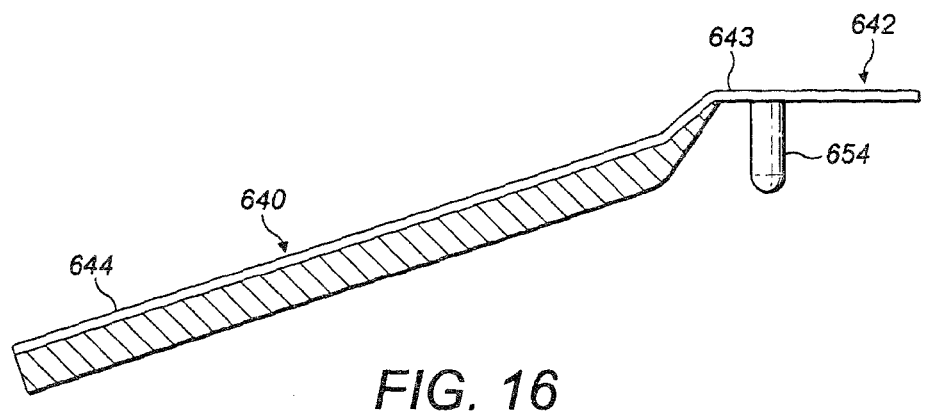
FIG. 16 is a view from above of the side blade shown in FIG. 14.

Finally, FIGS. 14, 15 and 16 illustrate a four-bladed speculum being an alternative to that shown in FIG. 12. Here, the side blades 640 lie on an inner side of the upper and lower blades 620, 630 when the upper and lower blades 620, 630 are in the closed position.

Each side blade 640 has a proximal root portion 643 and a distal free end portion 644 that moves laterally relative to the root portion 643. The free end portion 644 moves laterally by virtue of resilience of the side blade 640. For that purpose, the side blades 640 are shaped to be deformed elastically to fit the free end portion between the upper and lower blades 620, 630 when those blades 620, 630 are closed together. Specifically, in this example, the free end portion 644 is outwardly inclined relative to the root portion 643 in a distal direction. The elastic deformation is recovered when the upper and lower blades 620, 630 are moved apart into an open state, providing clearance for the free end portion 644 to spring out laterally from between the upper and lower blades 620, 630.

Each side blade 640 is connected to the lower blade 630 on an inner side of the lower blade 630 by means of a stud 645. The stud 645 is a protrusion extending laterally from the root portion 643 of the side blade 640 to be inserted into a recess in the spigot 631 of the lower blade 630.

The root portions 643 of each side blade 640 extend proximally into control levers 642 to position the side blades 640 as discussed in respect of the arrangement of FIG. 12.

In use, as the upper and lower blades 620, 630 move apart from one another, the side blades 640 are able to protrude laterally through the gap between the upper and lower blades 620, 630. The control levers 642 can be used to control the position of the side blades 640. As such, the side blades 640 can provide support against inward collapse of the vaginal wall between the opened upper and lower blades 620, 630 and provide a better view of the cervix or vaginal wall.

Many other variations are possible within the inventive concept. For example, whilst reference has been made to a spigot and a slot in respect of the first embodiment of the invention, it will be appreciated that any suitable coupling elements could be used. For instance, a recessed groove or an elongate cut-away within the side portion of the upper blade could be used in place of a slot. Furthermore, to minimise the risk of accidental disengagement of the blades 20, 30, a curved slot, an L-shaped slot, or one or more detent formations could be provided within the slot.

The use of an inclined slot 21 is an example of a detent that acts as a catch or stop providing resistance to discourage accidental decoupling of the coupling elements 21, 31. That resistance may easily be overcome to allow deliberate decoupling of the coupling elements 21, 31 when desired. In the embodiments illustrated, the resistance is provided by gravity acting on the upper blade 20 and also, in use of the speculum 10, by inward compressive force of the vagina. However, other detent arrangements are possible, such as a barrier or restriction in the slot 21 that must be broken, bypassed, deflected or surmounted by applying a release force for the spigot 31 to travel along the slot 21 to its open end.

It would also be possible for a breakable coupling element to be provided so that when a force greater than a threshold value is applied in a direction perpendicular to the pivot axis, the breakable coupling element breaks off to decouple the coupling elements and allow the blades 20, 30 to be separated.

Whilst the above embodiments of the invention utilise two coupling elements on each of the upper and lower blades, it will be appreciated that any number of coupling elements could be provided. For example, the upper and lower blades may each be provided with a single engaging element, which couple with one another to define the pivot axis.

It will be appreciated that references to the relative position of features of the speculum such as upper, lower, above, below, left, and right are not to be seen as limiting. These terms are used simply to help the reader to understand preferred features of the speculum.

The present invention may be embodied in other specific forms without departing from its essential attributes as defined in the appended claims and in other statements of invention herein. For example, the shape, size and material of the speculum can be selected to suit particular circumstances.

The invention claimed is:

1. A speculum for dilating a body cavity, the speculum comprising upper and lower blades arranged to pivot relative to each other about coupling elements each provided on a respective blade,
wherein the upper blade has a handle having a lower end,
wherein the lower blade has a handle having a lower end and a ratchet arm extending proximally from the lower end of the handle of the lower blade,
wherein the upper blade is detachable from the lower blade, when the speculum is in situ in the cavity, upon pulling the upper blade generally proximally to decouple the coupling elements from each other or to detach at least one of the coupling elements from the associated blade, and
wherein the coupling element of the upper blade is a slot that defines a path that is inclined relative to the upper blade upwardly and proximally when the speculum is oriented for use with the upper blade extending generally horizontally, and the coupling element of the lower blade is a spigot arranged to follow the path in a decoupling direction toward an open end of the path,
the speculum further comprising a locking mechanism acting between the handles to hold the blades open against inward pressure from the cavity, the locking mechanism being movable by a user to release the locking mechanism and free the blades for relative movement; the locking mechanism comprising the ratchet arm, the ratchet arm having an upper surface, a lower surface and teeth that engage the lower end of the handle of the upper blade to hold the blades open, and
wherein the coupling elements define a pivot axis; the ratchet arm further comprises a cantilever defined by parallel slits extending distally from the proximal end of the ratchet arm; the teeth are located on the cantilever; and the cantilever deflects resiliently away from pivot axis when the handles are brought together to open the blades.

2. The speculum of claim 1 and comprising a detent arranged to resist decoupling or detachment of at least one of the coupling elements, whose resistance must be overcome to effect decoupling or detachment, and wherein at least one of the coupling elements is arranged such that when the speculum is in situ in the cavity, the upper blade is guided to move upwardly when pulled proximally to decouple the coupling elements.

3. The speculum of claim 1, wherein the upper blade is detachable from the lower blade solely by pulling the upper blade away from the lower blade.

4. The speculum of claim 1, further comprising side blades positioned to resist inward movement of a wall of the cavity between the upper and lower blades when the speculum is in an open state.

5. The speculum of claim 4, wherein the side blades are coupled to the lower blade.

6. The speculum of claim 5, each of the side blades having a proximal root portion connected to an inner side of one of the lower blades, a distal free end portion and a control lever extending proximally from the root portion; wherein the side blades are coupled to the lower blade in pivoting manner such that the distal free end portions are movable in the vertical direction relative to the lower blade.

7. The speculum of claim 4, wherein the side blades are removably attached to the upper blade or the lower blade.

8. The speculum of claim 4, wherein the side blades are provided on an inner side of the upper and lower blades.

9. The speculum of claim 8, wherein the side blades are foaled from a resilient material, each of the side blades having a proximal root portion connected to an inner side of the lower blade and a distal free end portion that automatically moves laterally outward relative to the root portion by virtue of the resilience of the side blades when the upper and lower blades are moved apart into an open state.

10. The speculum of claim 9, wherein each of the side blades have a shape, set or curvature that deforms elastically to fit the free end portion between the upper and lower blades when those blades are closed together and that recovers elastically to move the free end portion laterally outward from between the upper and lower blades when those blades are moved apart into an open state.

11. The speculum of claim 1, further comprising an attachment feature on the lower blade for connecting the lower blade, in use, to body tissue within the cavity.

12. The speculum of claim 11, wherein the attachment feature is at or near a distal end of the lower blade.

13. The speculum of claim 11, wherein the attachment feature is a hole for attachment of a stitch extending into the body tissue or an aperture for receiving a protruding part of the body tissue or an aperture for accommodating a tenaculum extending through the aperture to the body tissue.

14. The speculum of claim 1, further comprising a line of weakness comprising perforations, grooves, notches or scores between at least one of the coupling elements and the associated blade, whereby the upper blade is detachable from the lower blade by detaching that coupling element from the associated blade along the line of weakness.

15. The speculum of claim 14, wherein the lower blade further comprises a pivot support extending proximally from the lower blade, and wherein the line of weakness is located on the pivot support.

16. The speculum of claim 1, wherein the teeth are disposed on the upper surface of the ratchet arm.

17. The speculum of claim 16, wherein the coupling elements define a pivot axis, and wherein the ratchet arm has a radius of curvature centred on the pivot axis.

18. The speculum of claim 1, wherein the teeth are disposed on the lower surface of the ratchet arm.

19. The speculum of claim 1, wherein the combination of the handle of the lower blade and the ratchet arm define a hook, the hook adapted to retain a weight to apply downward force to the lower blade when the speculum is in situ.

20. The speculum of claim 1, wherein the handle of the lower blade extends downwardly from the lower blade at an acute angle.

21. The speculum of claim 1, wherein the handle of the upper blade extends downwardly from the upper blade at an obtuse angle.

22. The speculum of claim 1, further comprising a tab extending proximally from the cantilever, wherein movement of the tab in the direction away from the pivot axis releases the handle of the upper blade from the teeth of the ratchet arm.

* * * * *